United States Patent

Vanlerberghe et al.

[11] Patent Number: 5,124,081
[45] Date of Patent: Jun. 23, 1992

[54] AMPHIPHILIC LIPID COMPOUNDS, PROCESS FOR THEIR PREPARATION AND THEIR APPLICATIONS ESPECIALLY IN COSMETICS AND DERMOPHARMACY

[75] Inventors: Guy Vanlerberghe, Claye-Souilly; Alexandre Zysman; Henri Sebag, both of Paris, all of France

[73] Assignee: L'Oreal, Paris, France

[21] Appl. No.: 877,766

[22] Filed: Jun. 24, 1986

[30] Foreign Application Priority Data

Jun. 25, 1985 [LU] Luxembourg ............... 85971

[51] Int. Cl.⁵ .................................. C09F 5/00
[52] U.S. Cl. .............................. 424/450; 424/70; 554/52; 554/56; 554/58; 554/59; 554/63
[58] Field of Search ............................ 260/404

[56] References Cited

U.S. PATENT DOCUMENTS

| | | | |
|---|---|---|---|
| 2,530,627 | 11/1950 | Pfister et al. | 562/567 |
| 4,150,024 | 4/1979 | Syldatk et al. | 260/239.3 |

FOREIGN PATENT DOCUMENTS

| | | |
|---|---|---|
| 0072286 | 2/1983 | European Pat. Off. |
| 83/01571 | 5/1983 | European Pat. Off. |
| 2657193 | 6/1978 | Fed. Rep. of Germany |
| 1477048 | 3/1967 | France |
| 2091156 | 1/1972 | France |
| 2315991 | 1/1977 | France |
| 2465780 | 3/1981 | France |
| 2482128 | 10/1983 | France |
| 874152 | 8/1961 | United Kingdom ............... 562/567 |
| 2059959 | 4/1981 | United Kingdom |

Primary Examiner—Bruce Gray
Attorney, Agent, or Firm—Cushman, Darby & Cushman

[57] ABSTRACT

Amphiphilic lipid compound having the formula:

$$R_1\text{—CHOH—CH—COA} \quad (I)$$
$$\underset{R_2\text{—CONH}}{|}$$

in which:
- $R_1$ denotes a $C_7$-$C_{21}$ alkyl or alkenyl radical,
- $R_2$ denotes a saturated or unsaturated $C_7$-$C_{31}$ hydrocarbon radical,
- COA denotes a group chosen from the following groups:
  a) COOM, M being H, Na, K, $NH_4$ or a substituted ammonium ion derived from an amine,
  b)

$$\underset{R}{\overset{}{|}}\text{CON—B.}$$

B being a radical derived from mono- or polyhydroxylated primary or secondary amines and R denoting a hydrogen atom or a methyl, ethyl or hydroxyethyl radical,
  c)

$$\underset{R}{\overset{}{|}}\text{CON—Q.}$$

Q denoting a substituted aminoalkyl or ammonioalkyl radical and R having the meaning indicated for b), and
  d) COOZ, Z representing the residue of a $C_3$-$C_7$ polyol, and a process for its preparation.

Cosmetic or dermopharmaceutical composition comprising the said compound and especially an aqueous dispersion of liposomes.

17 Claims, No Drawings

AMPHIPHILIC LIPID COMPOUNDS, PROCESS FOR THEIR PREPARATION AND THEIR APPLICATIONS ESPECIALLY IN COSMETICS AND DERMOPHARMACY

The present invention relates to new amphiphilic lipid compounds with a structure resembling that of sphingolipids which are found particularly in the skin, a process for their preparation, and their use, especially for skin and hair treatment and care in cosmetics or in dermopharmacy.

Exposure of skin to low temperatures, to sunlight, to atmospheres of low relative humidity, repeated treatments with washing compositions or contact with organic solvents are factors which, to various degrees, produce apparent drying. The skin appears drier, less supple and the skin texture more pronounced.

Similarly, hair which is too frequently subjected to certain hair treatments loses its shiny appearance and may become rough and brittle.

The applicants have therefore investigated compounds which make it possible to prevent or to correct these phenomena resulting in apparent drying and which restore to the skin its suppleness and its texture and to the hair its shine and its softness.

Thus, the applicants have found new compounds whose structure may be represented by the following formula:

$$R_1-CHOH-CH-COA \atop R_2-CONH \qquad (I)$$

in which:

$R_1$ denotes a $C_7$-$C_{21}$ alkyl or alkenyl radical $R_2$ denotes a saturated or unsaturated $C_7$-$C_{31}$ hydrocarbon radical optionally containing one or more hydroxyl groups and preferably one or two hydroxyl groups, and COA denotes a group chosen from the following:
a) COOM, M being H, Na, K, $NH_4$ or a substituted ammonium ion derived from an amine chosen preferably from hydroxyalkylamines such as mono-, di- or triethenolamine, mono-, di- or triisopropanolamine, 2-amino-2-methyl-1-propanol, 2-amino-2-methyl-1,3-propanediol or tris(hydroxymethyl)-aminomethane;

b) CONR-B,

B being a radical derived from mono- or polyhydroxylated primary or secondary amines such as for example: monoethanolamine, 2-amino-2-methyl-1-propanol, 2-amino-2-methyl-1,3-propanediol, N-methylethanolamine, diethanolamine, diglycolamine, glycerylamine, tris(hydroxymethyl)aminomethane, glucamine or 1-0-methyl-6-aminoglucose, and R denoting a hydrogen atom in the case of the primary amines and a methyl, ethyl or hydroxyethyl radical in the case of secondary amines;

c) CONR-Q,

R having the meanings indicated for b) and Q denoting a substituted aminoalkyl or ammonioalkyl radical such as, for example:

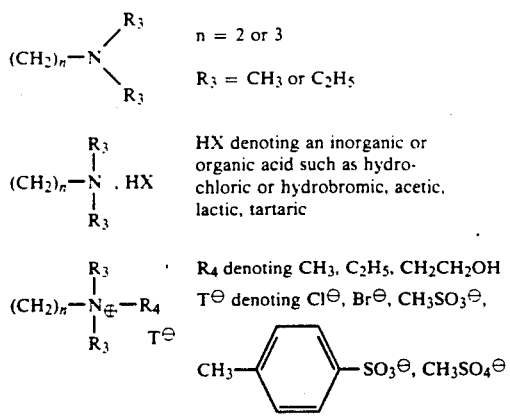

d) COOZ,

Z representing the residue of a $C_3$-$C_7$ polyol such as glycerol, glucose, methylglucose or sorbitol.

The above compounds (I), which in most cases exist in the form of waxes, enable certain apparent drying effects, especially on skin or hair, to be prevented or corrected.

These compounds, which enable skin and hair to be treated, are furthermore characterized by not being highly irritant to skin or to mucosa of the eye and by good tolerance by cell membranes such as those of erythrocytes. In addition, when combined with water-soluble surfactants, they enable the irritant properties to be appreciably reduced.

The new compounds of formula (I) are ionic or non-ionic amphiphilic substances which are characterized by a very good capacity for being dispersed in water, in most cases in the form of vesicles or liposomes. The products dispersed in this manner can facilitate the dispersion of cosmetic or pharmaceutical active substances having properties which are similar or complementary to theirs. These dispersions also form part of the invention.

The compounds according to the present invention thus constitute compounds which are of outstanding interest for skin and hair treatment, by virtue of their suppling and dispersing properties and their weak irritant properties.

The subject of the present invention is thus the new amphiphilic lipid compounds of formula (I) as defined above.

Another subject of the present invention consists of a process for the preparation of the compounds of formula (I) which is a multistage process which may be summarized by the following reaction scheme:

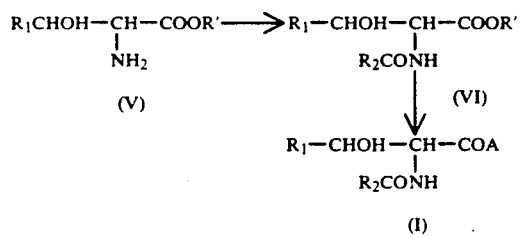

$R_1$, $R_2$ and A having the meanings indicated above and R' denoting $CH_3$ or $C_2H_5$.

In a first stage, the intermediate compounds containing two fatty chains of formula (VI) are prepared from compounds of formula (V), which are known compounds, obtained by conventional methods.

The former compounds are prepared by reaction of the compounds of formula (V) with:
- an acid chloride $R_2COCl$ in the presence of pyridine,
- an acid anhydride $R_2COOCOR_2$, prepared in situ in dimethylformamide, in the presence of cicyclohexylcarbodiimide, or
- an activated compound of the acid of formula:

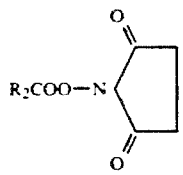

prepared in situ in dimethylformamide in the presence of dicyclohexylcarbodiimide and of N-hydroxysuccinimide.

In a second stage the compounds of formula (VI) are converted into compounds of formula (I) using conventional means.

The products of formula (Ia) according to the invention are obtained by saponifying and acidifying compounds (VI). If appropriate, the compounds obtained may then be neutralized with an alcoholate, an alkali or an amine.

The compounds (Ia) may also be obtained by acid hydrolysis of compounds (VI) and, if appropriate, neutralization.

The compounds (Ib) are obtained by an aminolysis reaction between the compounds (VI) and a mono- or polyhydroxylated primary or secondary amine such as one of the amines mentioned above in relation to formula (I) in the presence of a solvent such as hexane or toluene and, if appropriate, of a small quantity of sodium or potassium methylate or ethylate.

The compounds (Ic) are obtained from compounds (VI) by an aminolysis reaction with a primary-tertiary or secondary-tertiary diamine under conditions similar to those described for (Ib), if appropriate followed by a neutralization with an inorganic or organic acid or a quaternization with an alkylating agent such as a methyl or ethyl halide, dimethyl sulphate, methyl methanesulphonate or toluenesulphonate or glycol ghlorhydrin or bromohydrin.

The compounds (Id) are obtained by direct esterification of the acid (Ia) with a $C_3$-$C_7$ polyol or preferably by reaction with an epoxy derivative of the said polyol in the presence of an acidic or basic catalyst, or preferably also by reaction of a sodium, potassium or quaternary ammonium salt (Ia) with a methanesulphonic or p-toluenesulphonic ester of the said polyol.

The compounds (Id) may also be advantageously prepared by transesterification of the compounds (VI) with a $C_3$-$C_7$ polyol, optionally in the presence of an acidic or basic catalyst, and preferably under reduced pressure.

By way of example of a process for the preparation of compounds V, that summarized by the following reaction scheme may be mentioned:

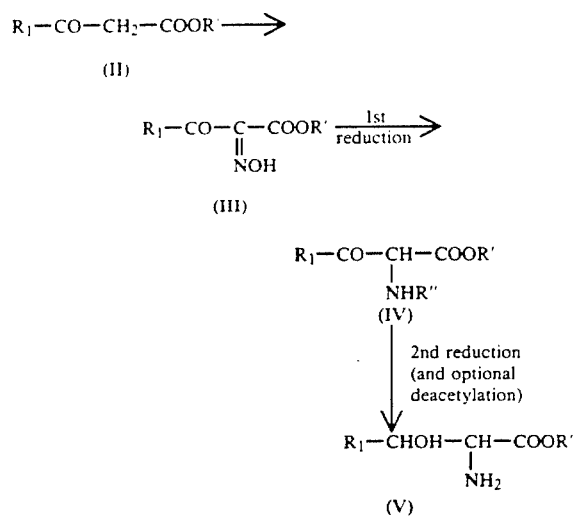

$R_1$ having the same meaning as above, R' denoting $CH_3$ or $C_2H_5$ and R" denoting a hydrogen atom or the acetyl radical.

The compounds of formula (II) are known compounds. These methyl or ethyl acetylacetates (II) are prepared by condensing an acid chloride $R_1COCl$ with the sodium derivative of ethyl acetylacetate (cf. "Chemistry of Sphingolipids", D. Shapiro, Hermann Paris 1969, page 21), followed by a deacetylation, according to the scheme:

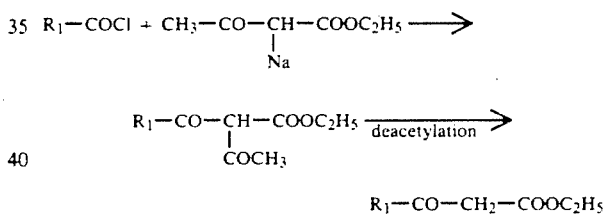

or by condensing the acid chloride $R_1COCl$ with Meldrum acid [cf. Roy P. Houghton and Daniel J. Lapham, "Synthesis" (1982), pages 451–452] according to the following reaction scheme:

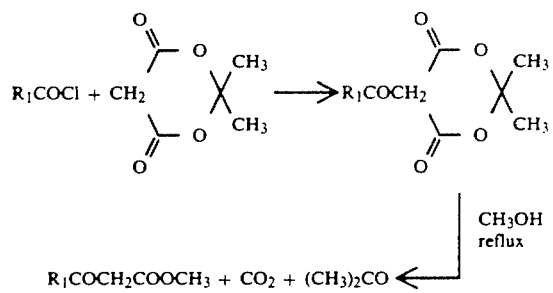

The compounds (III) are also known compounds, which are obtained by the reaction of butyl nitrite with the compounds (II) [D. Shapiro, "Chemistry of Sphingolipids", (1969), page 27].

The compounds of formula (V), which are known, are obtained by two successive reductions. The first reduction is performed either by catalytic hydrogenation over palladium [D. Shapiro, "Chemistry of Sphingolipids", (1969), page 27], or with zinc in the presence of acetic acid [D. Shapiro, "Chemistry of Sphingolipids", (1969), page 21], in which case a compound of formula (IV) in which R'=H is obtained, or with zinc in the presence of acetic acid and acetic anhydride, in which case a compound of formula (IV) in which R"=acetyl is obtained. The second reduction is performed in the presence of a borohydride, for example sodium borohydide NaBH$_4$ [D. Shapiro, "Chemistry of Sphingolipids", (1969), pages 21 and 41].

The intermediate compounds (V) are obtained after deacetylation, if appropriate, of the NH$_2$ group and neutralization.

The compounds according to the invention may be capable of a variety of applications, especially as dispersing or emulsifying agents or as waxy components in cosmetic and dermopharmaceutical compositions. In addition, they exhibit the property of forming vesicles or liposomes when they are dispersed in water.

A subject of the present invention is therefore the use of amphiphilic lipid compounds of formula (I) as emulsifying agents and waxy components of emulsions, and for the formation of liposomes.

Another subject of the present invention is compositions for cosmetic or dermopharmaceutical use in which a compound of formula (I) is present.

The compounds according to the invention may be in the form of emulsions (milk or cream), solutions (aqueous, aqueous-alcoholic, oily or oleoalcoholic), gels or dispersions or solid sticks.

According to the invention, the compounds of formula (I) represent 0.2 to 50%, and preferably 0.5 to 25%, of the total weight of the composition.

The compositions are, for example, emollient milks or creams, milks or creams for skin or hair care, creams or milks for removing makeup, makeup foundation bases, sun-protection milks or creams, milks or creams for artificial tanning and shaving creams or foams.

These compositions may also be in the form of lipsticks intended either for coloring the lips or for preventing chapping, or eye makeup products or face blushers and makeup foundations.

When the compositions according to the invention are in the form of emulsions of the water-in-oil or oil-in-water type, the fatty phase may essentially consist of a mixture of compounds of formula (I) with at least one oil and, if appropriate, at least one other wax.

The fatty phase of the emulsions may constitute 5 to 60% of the total weight of the emulsion.

The aqueous phase of the said emulsions preferably forms 30 to 85% of the total weight of the emulsion.

The proportion of the emulsifying agent may be between 1 and 20%, and preferably between 2 and 12% of the total weight of the emulsion.

The emulsifying agent may consist solely of the compound (I) according to the invention. The compound of formula (I) may also be associated with any other conventional emulsifier.

When the compositions according to the invention are in the form of aqueous solutions or dispersions, they may form products for washing or the treatment of skin and hair, or in the form of oily compositions such as, for example, sun-protection oils containing an UV-absorbent filter, softening oils for skin or for hair, foaming oils containing an oil-soluble surfactant, bath oils, and the like.

Among the main adjuvants which may be present in the compositions according to the invention there may be mentioned solvents such as water, lower monoalcohols or polyalcohols containing from 1 to 6 carbon atoms, or mixtures thereof; it is also possible to mention fatty substances such as mineral, animal or vegetable oils or waxes, fatty acids, fatty acid esters such as triglycerides of fatty acids containing from 6 to 12 carbon atoms, fatty alcohols and oxyethylenated fatty alcohols or polyglycerol alkyl ethers.

The particularly preferred mono- or poly-alcohols are chosen from ethanol, isopropanol, propylene glycol, glycerol and sorbitol.

As fatty substances, among the mineral oils, there may be mentioned vaseline oil; among animal oils, whale, seal, menhaden, halibut liver, cod, tuna, turtle, tallow, neat's foot, horse's hoof, sheep's foot, mink otter, marmot and similar oils; among vegetable oils, almond, peanut, wheatgerm, olive, maize germ, jojoba, sesame, sunflower, palm, walnut and similar oils.

Among fatty acid esters use may be made of esters of saturated or unsaturated $C_{12}$-$C_{22}$ acids and lower alcohols such as isopropanol or glycerol or linear or branched, saturated or unsaturated $C_8$-$C_{22}$ fatty alcohols or also $C_{10}$-$C_{22}$ 1,2-alkanediols.

As fatty substances there may also be mentioned vaseline, liquid paraffin, lanolin, hydrogenated lanolin, acetylated lanolin and silicone oils.

Among waxes there may be mentioned Sipol wax, lanolin wax, beeswax, candelilla wax, microcrystalline wax, carnauba wax, spermaceti, cocoa butter, karite butter, silicone waxes, hydrogenated oils which are solid at 20° C., sucroglycerides and Ca, Mg and Al oleates, myristates, linoleates and stearates.

Among fatty alcohols there may be mentioned lauryl, cetyl, myristyl, stearyl, palmityl and oleyl alcohols, among polyoxyethylenated fatty alcohols, lauryl, cetyl, stearyl and oleyl alcohols comprising from 2 to 20 moles of ethylene oxide, and among polyglycerol alkyl ethers, $C_{12}$-$C_{18}$ alcohols comprising from 2 to 10 moles of glycerol.

The composition according to the invention may also contain other ionic or nonionic amphiphilic agents.

It may also be useful to employ thickeners such as cellulose derivatives, polyacrylic acid derivatives, guar or carob gums or xanthane gum.

The composition according to the invention may also contain adjuvants which are usually employed in cosmetics or in dermopharmacy and especially hydrating products, emollients, products for the treatment of skin complaints, sunscreens, germicides, colorants, preserving agents, perfumes and propellants.

When the compositions according to the invention are dispersions, they are preferably aqueous spherule or liposome dispersions consisting of organized molecular layers enclosing an encapsulated aqueous phase, these layers consisting of at least one compound of formula (I).

Another subject of the present invention is therefore a dispersion of liposomes consisting of organized molecular layers of compounds(s) of formula (I) containing an aqueous phase to be encapsulated.

The continuous phase in the dispersion which surrounds the liposomes is an aqueous phase.

The dispersed liposomes or spherules are between 0.1 μm and 5 μm in diameter.

The aqueous phase encapsulated in the liposomes may be water or an aqueous solution of an active substance and in this case it is preferably isoosmotic with respect to the continuous phase of the dispersion.

The liposomes may be obtained in particular by following the process described in French Patent 2,315,991 of the applicant, according to which a dispersion of spherules consisting of organized molecular layers containing an aqueous phase to be encapsulated is prepared by bringing together, on the one hand one or more lipid compound(s) of formula (I) and, on the other hand, the aqueous phase to be encapsulated in the spherules, stirring to ensure mixing and to obtain a lamellar phase, then adding a dispersion liquid in a quantity greater than the quantity of the lamellar phase obtained and shaking vigorously for a period ranging from 15 minutes to approximately 3 hours.

The weight ratio of the aqueous phase to be encapsulated brought into contact with the compound(s) of formula (I) to the compound(s) of formula (I) forming the lamellar phase is preferably between 0.1 and 3.

The weight ration of the aqueous dispersion phase which is added, to the lamellar phase which is dispersed, is preferably between 2 and 100, the dispersion phase and the aqueous phase to be encapsulated being preferably isoosmotic.

Stirring is produced by means of a vibrating stirrer. The process is preferably carried out at a temperature of between 30° and 120° C. and preferably in the region of 70° C.

Another preparative process may consist in using the process known as REV (reverse-phase evaporation vesicle) or inverse phase evaporation, described in Proc. Natl. Acad. Sci. USA, Vol. 75, No. 9, pages 4194–4198); by Szoka and Papahedjopoulos.

The active substances which may be encapsulated in the aqueous phase may be substances of interest in the pharmaceutical or alimentary fields or substances possessing cosmetic activity.

The substances possessing cosmetic activity may be, for example, products intended for skin or hair care such as, for example, moisturizers such as glycerine, sorbitol, pentaerythritol, inositol, pyrrolidonecarboxylic acid and its salts; artificial tanning agents such as dihydroxyacetone, erythrulose, glyceraldehyde, γ-dialdehydes such as tartaric aldehyde, these compounds being, if appropriate, used in combination with colorants; water-soluble sunscreens; antiperspirants, deodorants, astringents, refreshing, tonic, cicatrizing, keratolytic or hair-removing agents; perfumed waters; animal or plant tissue extracts such as proteins, polysaccharides or amniotic fluid; water-soluble dyes; antidandruff agents; antiseborrhoeic agents, oxidizing agents such as bleaching agents like hydrogen peroxide; and reducing agents such as thioglycolic acid and its salts.

As pharmaceutical active substances there may be mentioned vitamins, hormones, enzymes such as superoxydase dismutase, vaccines, antiinflammatory agents such as hydrocortisone, antibiotics, bacteriocides and cytotoxic or antitumor agents.

In addition, various additives may be used in combination with the lipid compounds (I) in order to modify the permeability or the surface charge of the liposomes.

In this connection, there may be mentioned long-chain alcohols and diols, sterols such as cholesterol, phospholipids, cholesteryl sulphate and phosphate, long-chain amines and their quaternary ammonium derivatives, dihydroxyalkylamines, polyoxyethylenated fatty amines, long-chain aminoalcohol esters, their salts and quaternary ammonium derivatives, fatty alcohol phosphoric esters such as sodium dicetylphosphate, alkylsulphates such as sodium cetylsulphate, and certain polymers such as proteins or lipids of the type of those described in French Patents Nos. 2,315,991, 1,477,048 and 2,091,516 or in International Patent Application WO 83/01,571.

Among other lipids which may be used, for example, are lipids comprising a long, saturated or unsaturated, branched or linear chain containing 12 to 30 carbon atoms, for example an oleyl, lanolyl, tetradecyl, hexadecyl, isostearyl, lauryl or alkylphenyl chain. The hydrophilic group in these lipids may be an ionic or nonionic group, by way of ionic groups there may be mentioned the groups derived from polyethylene glycol. By way of ionic groups, a group derived from an amphoteric, anionic or cationic compound may be advantageously employed. It is also possible to use advantageously as lipids forming the lamellar phase polyglycerol ethers such as those described in French Patents Nos. 1,477,048, 2,091,516, 2,465,780 and 2,482,128.

Other lipids described in International Patent Application WO 83/01,571 as capable of being employed for the formation of liposomes are lipids containing oxidizable groups such as glycolipids like lastosylceramide, galactocerebroside, gangliosides and trihexosylceramide, as well as phospholipids such as phosphatidylglycerol and phosphatidylinositol.

Various adjuvants such as opacifying agents, gelling agents, flavorings, perfumed or colorants may also be added to liposome dispersions according to the invention.

The liposome dispersions according to the invention are of interest in permitting the introduction of hydrophilic active substances into an essentially lipophilic medium consisting of the compound of formula (I). These active substances are thus masked and protected against various agents capable of inducing a change: oxidizing agents and, more generally, compounds which are reactive towards the encapsulated active substances. The penetration and the fixation of the active substances may be modified by changing the size of the liposomes and their electric charge. The action of these active substances may also be delayed (delayed effect). Lastly, by virtue of the use of the lipids (I) according to the invention, and of associated active substances, it is possible to obtain a specific beneficial action which is specific for the active substance employed and which is at the same time suppling and of particular interest in the case of skin and hair treatment.

Another subject of the present invention is therefore the employment in cosmetics of an aqueous liposome dispersion consisting of organized molecular layers of lipid compounds (I) according to the invention enclosing an aqueous phase to be encapsulated, especially for skin or hair treatment.

Another subject of the invention is the use of such a liposome dispersion in dermopharmacy or in the food industry.

The present invention will be illustrated better by the following examples, not intended to imply any limitations.

EXAMPLE 1

Preparation of compound II with: $R_1 = C_{15}H_{31}$ and $R' = CH_3$ [methyl 3-oxooctadecanoate]

576 g (4 moles) of Meldrum acid (2,2-dimethyl-1,3-dioxane-4,6-dione) are dissolved in 2,400 cm³ of dichloromethane, all operations being carried out under nitrogen. After the solution has been cooled to 0° C., 640 cm³ of pyridine are added dropwise.

Still at the same temperature, 1,208 g (4.4 moles) of palmitoyl chloride are added over 1 hour, and then the reaction mixture is kept for another 1 hour at 0° C., with stirring. 6,000 cm³ of methanol are then added, still at 0° C., and the mixture is kept at this temperature for another 1 hour. It is left to stand overnight.

The mixture is heated under reflux for 5 hours. It is cooled, filtered and dried. 1,060 g of a white solid, m.p. = 55° C., are isolated.

Preparation of compound III with: $r_1 = C_{15}H_{31}$ and $R' = CH_3$ [methyl 2-oximino-3-oxooctadecanoate]

730 g (2.34 moles) of compound II are dissolved in 3.36 litres of ethyl ether and then 472 g (4.6 moles) of butyl nitrite are added.

The mixture is cooled to 0° C. 8.35 litres of a solution of hydrochloric acid in ether are added over 3 hours without exceeding 0° C. at any time.

The stirring is continued for 1 hour more at 0° C. and then the mixture is allowed to return to room temperature and is stirred for 1 hour.

The orange-colored solution is poured with stirring into 16 kg of water and ice. The ether phase is separated off and washed with 3 5-litre portions of water. The last wash should be virtually neutral.

The solvent phase is dried over sodium sulphate and is then evaporated down. 860 g of a pale yellow oil are obtained and this is recrystallized from 2 litres of hexane. After one night in the refrigerator the product is filtered and then washed with 2 200-ml portions of hexane. It is dried under vacuum. 495 g of a white solid, m.p.: 75° C., are isolated.

Preparation of compound V with: $R_1 = C_{15}H_{31}$ and $R' = CH_3$ [methyl 2-amino-3-hydroxyoctadecanoate]

490 g (1.43 mole) of compound III are dissolved in 3.85 litres of 100% acetic acid and then 2.3 litres of acetic anhydride are added. 470 g of zinc are added in small portions, with vigorous stirring, over 40 minutes. The temperature should not exceed 30° C. (if necessary cooling is applied using a waterbath). The reaction mixture is heated to 50° C. for 2 hours. It is then stirred for 2 hours longer at room temperature. 6.6 litres of water are gradually added while cooling with a bath of water and ice.

The cake of zinc and zinc acetate is filtered off and then washed with 2 600-ml portions of water. The filtrate is extracted with 3 3.5-litre portions of dichloromethane. The solvent extracts are washed with 2 1-litre portions of water and are then dried over sodium sulphate and evaporated to dryness.

640 g of product are obtained and recrystallized from 2.6 litres of acetone. After crystallization in the refrigerator, the product is filtered off and then washed with 2 300-ml portions of acetone. After drying, 415 g of a white solid, m.p.: 84° C., are isolated; this is methyl 2-acetamido-3-oxooctadecanoate.

410 g (1.1 mole) of methyl 2-acetamido-3-oxooctadecanoate are dissolved in 18 litres of methanol. The temperature needs to be raised to 28°–30° C. to achieve complete dissolution. The temperature is very gradually brought back to between 23° and 25° C. so as to avoid any initiation of crystallization of this solution. The following solution, prepared thus, is added over 10 minutes:

methanol 1.1 litre sodium methylate 4 meq (0.7 g of methylate containing 5.8 meq/g) to which mixture 28 g (0.74 mole) of sodium borohydride are added. The mixture is stirred for 40 minutes at room temperature. The solution is neutralized with concentrated acetic acid (approximately 15 ml) and then poured onto 10 kg of water and ice. A white precipitate forms.

The mixture is extracted with 3 3-litre portions of chloroform. The extracts are washed with 2 1.2-litre portions of water and are then dried over sodium sulphate. The solvent is evaporated off under vacuum.

After recrystallization from 1.840 litres of absolute ethanol, 258 g of methyl 2-acetamido-3-hydroxyoctadecanoate are isolated.

This is a white solid, with m.p. = 97° C.

250 g (0.67 mole) of methyl 2-acetamido-3-hydroxyoctadecanoate are dispersed in 1.8 litres of 10 N methanolic solution of hydrochloric acid. The dispersion is heated under reflux for 2 hours. After 30 minutes' refluxing, the starting product is seen to have dissolved.

After returning to ambient temperature, the majority of the solvent is evaporated off under vacuum. A potassium hydroxide trap has to be inserted in the vacuum line to trap the gaseous hydrogen chloride. Trituration with 4 litres of dry ether is carried out.

The crude hydrochloride is filtered off and is then washed with 2 300-ml portions of ether. It is recrystallized from 1.7 litres of isopropanol. 138 g of methyl 2-amino-3-hydroxyoctadecanoate hydrochloride are isolated.

This is a white solid, with m.p. = 72° C.

42 g of the methyl 2-amino-3-hydroxyoctadecanoate hydrochloride prepared above are dissolved in 250 cm³ of dichloromethane.

250 cm³ of a saturated $NaHCO_3$ solution are added to this solution and the mixture is stirred for 30 minutes. After phase separation the aqueous phase is extracted with 2 250-cm³ portions of dichloromethane and then the combined organic phases are washed with 2 250-cm³ portions of water. They are dried over sulphate and evaporated down. 35.5 g of methyl 2-amino-3-hydroxyoctadecanoate are collected.

32.9 g (0.1 mole) of the methyl 2-amino-3-hydroxyoctadecanoate prepared above are dissolved in 350 cm³ of dry dimethylformamide. 18 cm³ of pyridine are then added dropwise over 45 minutes at ambient temperature, followed by 28.3 g of technical grade oleoyl chloride (according to gas phase chromatography this contains 74% of oleoyl chloride, 23% of palmitoyl chloride and 3% of myristoyl chloride) dissolved in 180 cm³ of dry dimtheylformamide. Stirring is continued for 3 hours at ambient temperature.

The solvent is evaporated off under reduced pressure. The solid is washed several times with distilled water and is then dissolved in 1.5 litres of dichloromethane. The organic solution is washed again with 3 100-cm³ portions of water and is then dried over sodium sulphate. It is evaporated down and 57 g of a white solid with an m.p. of less than 50° C. are collected.

This is a mixture (A) of compounds corresponding to the following formula:

$$C_{15}H_{31}CHOHCHCOOCH_3 \atop \phantom{C_{15}H_{31}CHOH}NHCOR_2 \qquad (VI)$$

where $R_2$ denotes a mixture of hydrocarbon chains of formulae:

(CH₂)₇-CH═CH-(CH₂)₇-CH₃

(CH₂)₁₄ CH₃

(CH₂)₁₂ CH₃

¹³C NMR (DMSO-d6; TMS int. ref.; in ppm; Brucker WM 250)

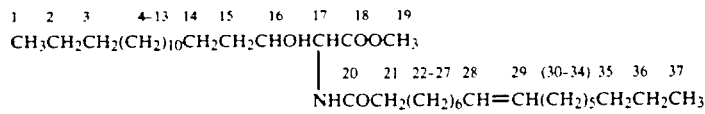

(The signals of the carbon atoms present in the saturated chains R₂ are indistinguishable from the corresponding signals of the above compound).

1+37:13.77; 2+36:21.98; 22:24.79; 14:25.95; 27+30:26.55; 4-13 and 23-27 and 30-34:28.59 to 28.96; 3+35: 31.20; 15:33.15; 21:34.95; 19:51.26; 17:57.19; 16:70.47; 28+29:129.5; 18+20:171.41 and 172.05

| Elemental analysis | | Calculated* | Found |
|---|---|---|---|
| *(for R₂: oleyl residue) | C | 74.12 | 74.38 |
| | H | 12.05 | 12.1 |
| | N | 2.36 | 2.32 |

EXAMPLE 2

The 57 g of mixture A prepared according to Example 1 are dissolved in 600 cm³ of 96° ethanol at 50° C. 110 cm³ of N NaOH are added over 10 minutes and stirring is continued for 1 hour longer at 50° C. The majority of the ethanol is then evaporated off and 120 cm³ of N HCL are added. The solid which precipitates is filtered off, washed with 3 100-cm³ portions of water and is then dried over P₂O₅.

After recrystallization from ethyl acetate, 50 g of a mixture (B) of compounds corresponding to the following formula are isolated:

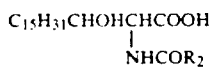

where R₂ retains the same meanings as those for mixture A in Example 1.

¹³C NMR (DMSO-d6).

Same signals as those of the final compound of Example 1, with the following differences:
1) absence of the signal of carbon no. 19 at 51 ppm
2) 18+20 at 172.00 and 172.28.

EXAMPLE 3

2 g of the mixture B prepared according to Example 2 are dissolved in 20 cm³ of isopropanol at 40° C. To this solution are added 5.8 g of a solution of sodium methylate in methanol at a concentration of 0.6 meq/g. The precipitated solid is filtered off and washed with 3 3-cm³ portions of isopropanol. 1.94 g of a mixture of compounds corresponding to the following formula are isolated:

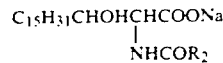

where R₂ retains the same meanings as those for mixture B in Example 2.

EXAMPLE 4

38 g of the mixture B prepared according to Example 2 are dissolved in 225 cm³ of absolute ethanol at 45° C.

To this solution are added 12.12 g of triisolpropanolamine dissolved in 50 cm³ of absolute ethanol. The solvent is then removed by evaporation under reduced pressure. 50 g of a solid melting at about 60° C. are isolated.

This is a mixture of compounds corresponding to the formula:

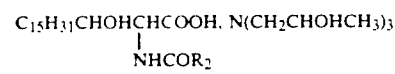

where R₂ retains the same meanings as those for mixture B in Example 2.

EXAMPLE 5

25 g of the mixture B prepared according to Example 2 are dissolved in 300 cm³ of methanol. To this solution are added 100 cm³ of a methanolic solution containing 3.34 g of monoisopropanolamine. The solvent is then removed under reduced pressure. 28.2 g of a white solid melting at about 94° C. are isolated.

This is a mixture of compounds corresponding to the formula:

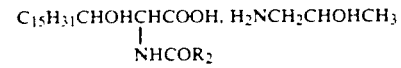

where R₂ retains the same meanings as those for the mixture B in Example 2.

EXAMPLE 6

4.2 g (0.036 M) of N-hydroxysuccinimide are dissolved in 250 cm³ of dry dimethylformamide. 9.37 g (0.0334 mole) of linoleic acid are added to this solution over 15 minutes. The temperature of this solution is lowered to 0° C. and then 7.52 g (0.036 mole) of dicyclohexylcarbodiimide are added to it over 20 minutes, in small portions. Stirring is continued for 2 hours at 0° C. After returning to ambient temperature, 10 g (0.0304 mole) of methyl 2-amino-3-hydroxyoctadecanoate, prepared according to Example 1, are added over 30 minutes.

The mixture is kept stirred overnight. The dicyclohexylurea formed is removed by filtration. The solvent is removed by evaporation under reduced pressure.

The residue is subjected to chromatography under pressure:
(phase: silica 60 H Merck Art. 7736;

eluent: $CH_2cl_2:CH_3OH = 95:5$;
elution pressure: 8 bars).

11 g of methyl 2-linoleyl amino-3-octadecanoate are isolated.

This is a white solid with m.p. = 56° C.

$^{13}C$ NMR (same conditions as in Example 1 but in $CDCl_3$).

$$\begin{array}{c} \overset{1}{C}H_3\overset{2}{C}H_2\overset{3}{C}H_2\overset{4-13}{(CH_2)_{10}}\overset{14}{C}H_2\overset{15}{C}H_2\overset{16}{C}HOH\overset{17}{C}H\overset{18}{C}OO\overset{19}{C}H_3 \\ | \\ \overset{20}{N}H\overset{21}{C}O\overset{22}{C}H_2\overset{23-27}{C}H_2(CH_2)_5 \overset{28}{C}H=\overset{29}{C}H-\overset{30}{C}H_2-\overset{31}{C}H=\overset{32}{C}H\overset{33}{C}H_2\overset{34}{C}H_2\overset{35}{C}H_2\overset{36}{C}H_2\overset{37}{C}H_3 \end{array}$$

1 37:14.07 and 14.12; 36:22.59; 2:22.71; 14+22+30:25.58-25.68-25.74; 27+33:27.24; 4 to 13+23 to 26+34:29.16 to 29.71; 35:31.56; 3:31.95; 15:33.44; 21:36.44; 19:52.54; 17:57.65; 16:73.21; 31; 127.93; 29:128.09; 28:130.01; 32:130.21; 20:171.00; 18:173.91.

EXAMPLE 7

5 g of methyl 2-linoleoylamino-3-hydroxyoctadecanoate prepared according to Example 6 are dissolved in 200 cm³ of 96° ethanol.

To this solution are added 7 g of $K_2CO_3$ dissolved in 10 cm³ of water. The solution is kept at 60° C. for 2 hours.

The majority of the alcohol is then evaporated off and the residue is acidified with a N solution of HCl. The solid precipitate is filtered off and washed several times with water. After drying over $P_2O_5$, 4.5 g of a white solid with m.p. of 81.5° C. are isolated.

This is 2-lineolamino-3-hydroxyoctadecanoic acid.

$^{13}C$ NMR Same signals as those of the end compound in Example 6, with the following differences:
1) disappearance of the signal of C no. 19 at 52.54 ppm
2) 20:171.9 and 18:175.19

EXAMPLE 8

To 2 g of 2-linoleoylamino-3-hydroxyoctadecanoic acid, prepared according to Example 7 and dissolved in 100 cm³ of methanol are added 5 cm³ of a methanolic solution containing 0.26 g of monoisopropanolamine.

The solvent is removed by distillation under reduced pressure. 2.2 g of a solid melting at 96° C. are isolated. This corresponds to the formula:

$$\begin{array}{c} C_{15}H_{31}CHOHCHCOOH, \ H_2NCH_2CHOHCH_3 \\ | \\ NHCO(CH_2)_7CH=CHCH_2CH=CH(CH_2)_4CH_3 \end{array}$$

EXAMPLE 9

1.48 g (0.0168 mole) of dimethylaminoethylamine are added to 3.34 g of mixture A prepared according to Example 1 and dissolved in 15 cm³ of hexane. The reaction mixture is heated under reflux for 4 hours. The solvent is evaporated off under reduced pressure. The solid obtained is taken up with dichloromethane and is washed several times with water.

After drying over sodium sulphate and after evaporation of the solvent, 3 g of a white solid melting at about 86° C. are isolated.

This is a mixture of compounds corresponding to the following formula:

$$\begin{array}{c} \quad\quad\quad\quad\quad\quad\quad\quad CH_3 \\ \quad\quad\quad\quad\quad\quad\quad / \\ C_{15}H_{31}CHOHCHCONHCH_2CH_2N \\ | \quad\quad\quad\quad\quad\quad\quad \backslash \\ NHCOR_2 \quad\quad\quad\quad\quad CH_3 \end{array}$$

where $R_2$ retains the same meanings as those for mixture A in Example 1.

| Elemental analysis | | Calculated* | Found |
|---|---|---|---|
| *Cf. Example 1 | C | 73.86 | 73.74 |
| | H | 12.30 | 12.40 |
| | N | 6.46 | 6.43 |

$^{13}C$ NMR ($CDCl_3$)

$$\begin{array}{c} \quad\quad\quad\quad\quad\quad\quad\quad\quad\quad\quad\quad\quad\quad\quad\quad\quad \overset{21}{C}H_3 \\ \quad\quad\quad\quad\quad\quad\quad\quad\quad\quad\quad\quad\quad\quad\quad\quad / \\ \overset{1}{C}H_3\overset{2}{C}H_2\overset{3}{C}H_2\overset{4-13}{(CH_2)_{10}}\overset{14}{C}H_2\overset{15}{C}H_2\overset{16}{C}HOH\overset{17}{C}H\overset{18}{C}O\overset{19}{N}H\overset{20}{C}H_2\overset{}{C}H_2N \\ \quad\quad\quad\quad\quad\quad\quad\quad\quad\quad\quad\quad\quad\quad\quad\quad\quad \backslash \overset{22}{} \\ \quad\quad\quad\quad\quad\quad\quad\quad\quad\quad\quad\quad\quad\quad\quad\quad\quad\quad CH_3 \\ | \\ \overset{23}{N}H\overset{24}{C}O\overset{25-30}{C}H_2(CH_2)_6\overset{31}{C}H=\overset{32}{C}H(CH_2)_5\overset{38}{C}H_2\overset{39}{C}H_2\overset{40}{C}H_3 \end{array}$$

1+40:14.12; 2+39:22.69; 14+25:22.65 and 25.89; 30+33:27.22; 4 to 13 and 26 to 29:near 29.72; 3+38:31.93; 15:33.81; 24:36.4; 19:36.5; 21+22:44.74; 17:57.19; 20:57.75; 16:73.28; 31+32:129.69 and 129.96; 18+23:171.17 and 173.65.

EXAMPLE 10

2 g of the mixture of compounds prepared according to Example 9 are dissolved in 50 cm³ of methanol. To this solution is added a solution containing 0.28 g of lactic acid in a mixture of water and alcohol. The solvent is evaporated off under reduced pressure and 2.2 g of a white solid melting at about 51° C. are isolated. This mixture corresponds to the formula:

$$\begin{array}{c} C_{15}H_{31}CHOHCHCONHCH_2CH_2N(CH_3)_2, \ HOOCCHOHCH_3 \\ | \\ NHCOR_2 \end{array}$$

where $R_2$ retains the same meanings as those for the mixture in Example 9.

EXAMPLE 11

5.28 g (0.44 M) of tris(hydroxymethyl)aminomethane are dissolved in 50 cm³ of dry dimethylformamide. To this solution are added 4.15 g (0.007 mole) of the compound prepared in Example 6 and dissolved in 50 cm³ of dry dimethylformamide. 3 drops of sodium methylate (at a concentration of 5.5 meq/g) are added to the reaction mixture which is then heated to 80° C. Heating is maintained for 15 hours. The solvent is then evaporated off under reduced pressure and a separation on a silica column is then carried out (silica: Lichroprep Si 60 40–63 μm; eluent: $CH_3Cl_2:CH_3OH = 96:4$; elution pressure: 4 bars.

5 g of a white solid are isolated. Melting point: 134° C. This corresponds to the formula:

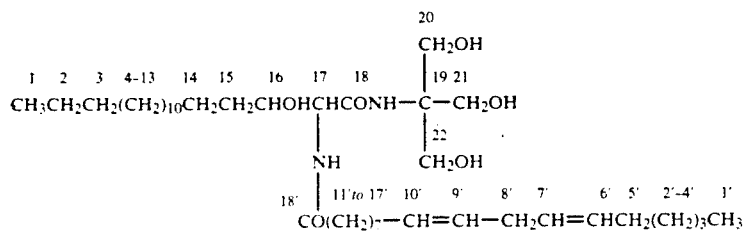

$^{13}C$ NMR (CDCl₃).

1+1':14.06; 2':22.6; 2:22.71; 14+16'+8':25.74; 5'+11'27.28; 4 to 13 and 12' to 15':29.32 to 29.78; 3':31.59; 3:31.98; 15:33.96; 17':36.56; 17:57.90; 20+21+22:62.55; 19:63.38; 16:72.80; 7':128.01; 9':128.25; 10':130.02; 6':130.32; 18+18':172.51 and 174.62.

EXAMPLE 12

10.7 g (0.033 mole) of methyl 2-amino-3-hydoxyoctadecanoate prepared according to Example 1 are dissolved in 200 cm³ of dry benzene and then 3.28 g of triethylamine are added. 8.92 g (0.033 mole) of palmitoyl chloride dissolved in 60 cm³ of benzene are added dropwise to this solution between 20 and 35° C. After 3 hours' stirring, the triethylamine hydrochloride is removed by filtration at 40° C. The organic phase is washed twice with 100 cm³ of water. The benzene solution is dried over sodium sulphate and then part of the benzene is removed by evaporation. 16.3 g of methyl 2-hexadecanoylamino-3-hydroxyoctadecanoate are isolated by crystallization.

This is a white solid, with m.p.=80° C.
$^{13}C$ NMR

```
 1   2   3   4-13  14  15  16   17  18   19
CH3CH2CH2(CH2)10CH2CH2CH—CHCOOCH3
                         |   |
                         OH  NHCOCH2CH2(CH2)10CH2CH2CH3
                             20 21   22  23-32   33  34  35
```

1+35:14.12; 2+34:22.7; 14+22:25.6 and 25.72; 4 to 13 and 23 to 32:29.24 to 29.7; 3+33:31.93; 15:33.37; 21:36.44; 19:52.57; 17:57.66; 16:73.2; 20:170.99; 18:173.99.

EXAMPLE 13

15 g of methyl 2-hexadecanoylamino-3-hydroxyoctadecanoate prepared according to Example 12 are dissolved in 225 cm³ of ethanol. 32 cm³ of normal sodium hydroxide solution are added to this solution and the mixture is heated with stirring for 1 hour at 50° C. A white solid precipitates during the reaction and is isolated by filtration. After washing and then drying, 15.5 g of a white solid, which does not melt even at 250° C., are isolated.

Its basicity value, measured using perchloric acid in acetic acid, is 1.65 meq/g.

This is a sodium salt of 2-hexadecanoylamino-3-hydroxyoctadecanoic acid.

EXAMPLE 14

12.5 g of the sodium salt of 2-hexadecanoylamino-3-hydroxyoctadecanoic acid prepared according to Example 13 are dispersed in 100 cm³ of water. To this dispersion are added 500 cm³ of ethyl acetate followed by 5 cm³ of 11 N HCL. The two phases are separated at 40° C. The organic phase is washed with 100 cm³ of water and is then dried. It is partially concentrated and, when cooled, it then yields 9.9 g of a white solid.

This melts at 140° C. Its acid value is 1.82 meq/g; it is 2-hectadecanoylamino-3-hydroxyoctadecanoic acid.

EXAMPLE 15

2.05 ml of a 35% solution of butyltrimethylammonium hydroxide (Triton B) in methanol are added to 2.35 g of mixture B obtained according to Example 2 and dissolved in 30 cm³ of isopropanol dried over a molecular sieve.

The isopropanol is distilled under a vacuum of 15 mm Hg while the temperature is maintained at a maximum of 40° C., to dryness. The product obtained is taken up with 30 cm³ of dry dimethylformamide and to this solution are added 1.39 g of 6-tosylate-1-methylglucose dissolved in 10 cm³ of dimethylformamide and the temperature is raised to 80° C.

After being heated at this temperature for 7 hours, the solution is filtered through sintered glass and is concentrated at 80° C. at a vacuum of 0.5 mm Hg. The mixture obtained is treated by HPLC on a Kieselgel 60 H silica column with a 90:10 dichloromethane:isopropanol eluent.

1.39 g of pale yellow waxy product which melts at about 65° C. are isolated. It shows a spot at $R_f$ of 0.7 in thin-layer chromatography on silica using a 90:10 dichloromethane:isopropanol system as eluent.

This compound corresponds to the following formula:

$$\begin{array}{c}\text{C}_{15}\text{H}_{31}\text{CHOHCHCOO}\\|\quad\quad\quad|\\\text{R}_2\text{CONH}\quad\text{CH}_2\end{array}$$

(sugar ring with OH, OH, OH, OCH₃)

where $R_2$ retains the same meanings as those for mixture A in Example 1.

EXAMPLE 16

2.11 g (0.018 mole) of hydroxysuccinimide are dissolved in ethyl acetate at 50° C. At this temperature, 5 g (0.018 mole) of 16-hydroxyhexadecanoic acid are added to the solution, followed by 3.79 g (0.018 mole) of N,N'-dicyclohexylcarbodiimide, both dissolved beforehand in 10 ml of ethyl acetate. The stirring is maintained at 50° C. for 5 hours and then the reaction medium is filtered hot in order to remove the dicyclohexylurea formed. On cooling, the filtrate yields 4.5 g of an activated ester corresponding to the formula:

(succinimidyl ester: NOC(CH₂)₁₅OH)

The structure of this ester is established by $^1$H NMR.

3 g (0.0091 mole) of methyl 2-amino-3-hydroxyoctadecanoate prepared according to Example 1 are dissolved in 100 cm³ of tetrahydrofuran. 3.36 g (0.0091 mole) of the above activated ester are dissolved separately in 100 cm³ of the same solvent and the two solutions are mixed. The reaction mixture is stirred at ambient temperature for 4 hours and then the solvent is evaporated off. The solid obtained is recrystallized twice from approximately 20 cm³ of tetrahydrofuran. 4.1 g of a white solid, with m.p. = 80° C., are isolated.

This corresponds to the formula below:

$$\begin{array}{c}{}^{16}\quad {}^{17}\;{}^{18}\;{}^{19}\\ \text{C}_{15}\text{H}_{31}\text{CHOHCHCOOCH}_3\\|\\{}^{20}\quad\;{}^{35}\\\text{NHCO(CH}_2)_{14}\text{CH}_2\text{OH}\end{array}$$

The characteristic signals in $^{13}$C NMR (CDCl₃) are as follows:
16:72.55 and 71.54; 17:57.38 and 56.40;
18 and 20:171.25+172.18+174.57+174.78; 19:52.47 and 52.37; 35:62.59.

1 g of the above compound is dissolved in 20 ml of 96° C. alcohol at 60° C. and then 3 cm³ of normal sodium hydroxide solution are added. The solution is heated for 2 hours at 60° C. On cooling, the solution yields 0.8 g of a white solid. Basicity value: 1.7 meq/g (CH₃OH/HCl).

This corresponds to the following formula:

$$\begin{array}{c}{}^{16}\quad {}^{17}\;{}^{18}\\ \text{C}_{15}\text{H}_{31}\text{CHOHCHCOONa}\\|\\{}^{19}\quad\;{}^{34}\\\text{NHCO(CH}_2)_{14}\text{CH}_2\text{OH}\end{array}$$

The characteristic signals in $^{13}$C NMR (CD₃OD) are as follows:
16:74.46 and 73.33; 17:60.70 and 59.35; 18 and 19:177.69+176.65+176.25+175.60; 34:63.09.

EXAMPLE 17

The activated ester of 2-hydroxyhexadecanoic acid, which corresponds to the formula below:

(succinimidyl ester: NOC–CHOHC₁₄H₂₉)

is prepared using the same conditions as in Example 16.

3.19 g (0.0086 mole) of the above ester are dissolved in 10 ml of dry tetrahydrofuran. 2.84 g (0.0086 mole) of methyl 2-amino-3-hydroxyoctadecanoate are dissolved separately in 100 ml of the same solvent and the two solutions are mixed. The solution is stirred at ambient temperature for 18 hours. The solvent is evaporated off under reduced pressure and the solid obtained is purified by preparative chromatography under pressure (Merck 60 silica; CH₂Cl₂:CH₃OH=9:1).

3 g of a white solid, with m.p. = 82° C., are isolated. This corresponds to the formula:

$$\begin{array}{c}{}^{16}\quad {}^{17}\;{}^{18}\;{}^{19}\\ \text{C}_{15}\text{H}_{31}\text{CHOHCHCOOCH}_3\\|\\{}^{20}\;{}^{21}\\\text{NHCOCHOH(CH}_2)_{13}\text{CH}_3\end{array}$$

The characteristic signals in $^{13}$C NMR (CDCl₃) are as follows:
16 and 21:72.87+72.36+71.64; 17:57.20+56.06+55.84; 19:52.69 and 52.56; 18 and 20:175.23+172.43+171.91+171.15+170.64.

2.1 g of the above compound are dissolved in 200 ml of 96° alcohol at 60° C. and 7 ml of normal sodium hydroxide solution are added. The solution is heated at this temperature for 4 hours. On cooling, the solution yields a white solid, which is recrystallized from a mixture of 250 ml of alcohol and 25 ml of water. Basicity value: 1.67 meq/g (CH₃COOH/HClO₄).

This corresponds to the following formula:

$$\begin{array}{c}{}^{16}\quad {}^{17}\;{}^{18}\\ \text{C}_{15}\text{H}_{31}\text{CHOHCHCOONa}\\|\\{}^{19}\;{}^{20}\\\text{NHCOCHOH(CH}_2)_{13}\text{CH}_3\end{array}$$

The characteristic signals in $^{13}$C NMR (CD₃COOD) are as follows:
16+20:73.17+72.93+72.53+72.36; 17:57.66+56.72
18 and 19 are obscured by the solvent.

EXAMPLES OF APPLICATION

Example 1

Liquid for care of aged skins

The following aqueous dispersion is prepared first:
Ionic amphiphilic lipid of formula:

| | |
|---|---|
| (compound of Example 5) | 4.8 g |
| Cholesterol | 3.2 g |
| Methyl para-hydroxybenzoate | 0.3 g |
| Hydroxyproline | 0.7 g |
| Demineralized water | 62.8 g |
| 20% strength aqueous solution of collagen proteins marketed by the Croda company under the name "Nutrilan I" (MW 1.000) | 7.0 g |

The following substances are then added:

| | |
|---|---|
| Perfume | 0.4 g |
| Mixture of vinylcarboxylic acids marketed under the name of Carbopol 940 | 0.4 g |
| Triethanolamine | 0.4 g |
| Demineralized water | 20.0 g |

When applied to the skin, this liquid makes it soft and smooth.

EXAMPLE 2

Cream for care of dry skins

An aqueous dispersion containing the following is prepared in a first stage:

| | |
|---|---|
| (compound of Example 5) | 4.8 g |
| Cholesterol | 3.2 g |
| Methyl para-hydroxybenzoate | 0.3 g |
| Glycerine | 3.0 g |
| Demineralized water | 42.5 g |

In a second stage,

| | |
|---|---|
| Sesame oil | 25.0 g | is added to the above aqueous dispersion.

The whole is subjected to mechanical stirring so that the external phase of the dispersion forms an oil-in-water emulsion.

Lastly, the following substances are added:

| | |
|---|---|
| Perfume | 0.4 g |
| Mixture of vinylcarboxylic acids marketed under the name of Carbopol 940 | 0.4 g |
| Triethanolamine | 0.4 g |
| Demineralized water | 20.0 g |

This cream imparts softness to dry skins.

We claim:

1. An amphiphilic lipid compound having the formula

wherein $R_1$ represents a $C_7$-$C_{21}$ alkyl or alkenyl radical, $R_2$ represents a saturated or unsaturated $C_7$-$C_{31}$ hydrocarbon radical or a saturated or unsaturated $C_7$-$C_{31}$ hydrocarbon radical or a saturated or unsaturated $C_7$-$C_{31}$ hydrocarbon radical bearing one or more hydroxyl groups, and COA represents COOM wherein M is H, Na, K, NH$_4$ or a substituted ammonium ion derived from an amine.

2. An amphiphilic lipid compound having the formula

wherein $R_1$ represents a $C_7$-$C_{21}$ alkyl or alkenyl radical, $R_2$ represents a saturated or unsaturated $C_7$-$C_{31}$ hydrocarbon radical or a saturated or unsaturated $C_7$-$C_{31}$ hydrocarbon radical bearing one or more hydroxyl groups, and COA represents (a) COOM wherein M is H, Na, K, NH$_4$ or a substituted ammonium ion derived from an amine or (b) COOZ wherein Z represents the residue of a $C_3$-$C_7$ polyol.

3. An amphiphilic lipid compound having the formula

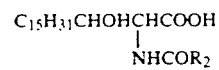

wherein $R_2$ represents a hydrocarbon chain of the formula: —(CH$_2$)$_7$—CH=CH—(CH$_2$)$_7$—CH$_3$.

4. An amphiphilic lipid compound having the formula:

$R_1$ represents $C_7$-$C_{21}$ alkyl or $C_7$-$C_{21}$ alkenyl, $R_2$ represents a saturated or unsaturated $C_7$-$C_{31}$ hydrocarbon radical or a saturated or unsaturated $C_7$-$C_{31}$ hydrocarbon radical substituted with at least one hydroxyl group, COA represents a radical selected from the group consisting of (a) COOM wherein M represents H, Na, K, NH$_4$ or a substituted ammonium ion derived from an amine, (b)

wherein B is a radical derived from a mono- or polyhydroxylated primary or secondary amine, and R represents hydrogen, methyl, ethyl or hydroxyethyl, (c)

wherein Q represents a substituted aminoalkyl or ammonioalkyl radical, and R has the meaning indicated in (b) above, and (d) COOZ wherein Z represents the residue of a $C_2$-$C_7$ polyol.

5. The compound of claim 4 wherein COA represents COOM wherein M represents H, Na, K, $NH_4$ or a substituted ammonium ion derived from a hydroxyalkylamine selected from the group consisting of mono-, di- or triethanolamine, mono-, di- or triisopropanolamine, 2-amino-2-methyl-1-propanol, 2-amino-2-methyl-1,3-propane diol and tris(hydroxymethyl) aminomethane.

6. The compound of claim 4 wherein COA represents COOZ wherein Z represents the residue of a $C_3$-$C_7$ polyol selected from the group consisting of glycerol, glucose, methyl glucose and sorbitol.

7. A composition for the treatment of hair or skin so as to prevent or correct the drying of the hair or skin, said composition comprising in a medium suitable for application to said hair or skin, the amphiphilic lipid compound of claim 4 present in an amount ranging from 0.2 to 50 percent by weight based on the total weight of said composition.

8. The composition of claim 7 wherein said amphiphilic lipid compound is present in an amount ranging from 0.5 to 25 percent by weight based on the total weight of said composition.

9. The composition of claim 7 in the form of an emulsion comprising an oily phase, an aqueous phase, and an emulsifying agent, said oily phase constituting 5 to 60 weight percent of said emulsion and comprising a mixture of said amphiphilic compound and at least one oil, said aqueous phase constituting 30-85 weight percent of said emulsion, and said emulsifying agent comprising said amphiphilic lipid compound present in an amount ranging from 1 to 20 percent by weight based on the total weight of said emulsion.

10. The composition of claim 9 wherein said emulsifying agent is present in an amount ranging from 2 to 12 percent by weight based on the total weight of said emulsion.

11. The composition of claim 7 in the form of an aqueous solution, an aqueous-alcoholic solution, an oily solution, an oleoalcoholic solution, a gel or a dispersion.

12. The composition of claim 7 in the form of a solid stick.

13. The composition of claim 7 in the form of a dispersion of spherules or liposomes surrounded by a continuous aqueous phase, said spherules or liposomes comprising organized molecular layers of said amphiphilic lipid compound and encapsulating an aqueous phase selected from water or an aqueous solution of an active product.

14. The composition of claim 13 wherein said aqueous phase encapsulated in said spherules or liposomes is an aqueous solution of an active substance which is isoosmotic relative to said continuous aqueous phase surrounding said spherules or liposomes.

15. The composition of claim 13 wherein the diameter of said spherules or liposomes ranges from 0.1 μm to 5 μm.

16. The composition of claim 13 wherein the aqueous phase encapsulated in said spherules or liposomes contains a cosmetically active adjuvant.

17. The composition of claim 13 wherein the aqueous phase encapsulated in said spherules or liposomes contains a dermopharmaceutically active substance.

* * * * *